(12) United States Patent
Fujieda et al.

(10) Patent No.: US 7,296,896 B2
(45) Date of Patent: Nov. 20, 2007

(54) OPHTHALMIC MEASUREMENT APPARATUS

(75) Inventors: Masanao Fujieda, Toyohashi (JP); Yukinobu Ban, Nishio (JP)

(73) Assignee: Nidek Co., Ltd., Aichi (JP)

( * ) Notice: Subject to any disclaimer, the term of this patent is extended or adjusted under 35 U.S.C. 154(b) by 76 days.

(21) Appl. No.: 11/346,382

(22) Filed: Feb. 3, 2006

(65) Prior Publication Data

US 2006/0192920 A1 Aug. 31, 2006

(30) Foreign Application Priority Data

Feb. 4, 2005 (JP) .............................. 2005-029893

(51) Int. Cl.
*A61B 3/10* (2006.01)

(52) U.S. Cl. ................. 351/214; 351/205; 351/206

(58) Field of Classification Search ............... 351/205, 351/206, 208–210, 214, 221
See application file for complete search history.

(56) References Cited

U.S. PATENT DOCUMENTS

| | | | |
|---|---|---|---|
| 4,526,451 A | | 7/1985 | Nohda |
| 5,907,388 A | | 5/1999 | Fujieda |
| 6,033,075 A | | 3/2000 | Fujieda et al. |
| 6,056,404 A | * | 5/2000 | Kawai et al. ................ 351/237 |
| 6,079,828 A | * | 6/2000 | Fujieda ....................... 351/206 |
| 6,382,796 B1 | * | 5/2002 | Ban ............................ 351/212 |
| 6,467,907 B1 | * | 10/2002 | Fujieda et al. ............. 351/212 |
| 6,536,900 B2 | | 3/2003 | Mihashi et al. |
| 2003/0163122 A1 | | 8/2003 | Sumiya |

FOREIGN PATENT DOCUMENTS

| | | |
|---|---|---|
| JP | A 57-165735 | 10/1982 |
| JP | A 10-108837 | 4/1998 |
| JP | A 2001-275972 | 10/2001 |
| JP | A 2001-524662 | 12/2001 |
| JP | A 2003-245300 | 9/2003 |
| WO | WO99/27334 | 6/1999 |

* cited by examiner

*Primary Examiner*—Huy Mai
(74) *Attorney, Agent, or Firm*—Oliff & Berridge, PLC

(57) ABSTRACT

An ophthalmic measurement apparatus capable of obtaining refractive power containing a skew ray component, and further obtaining wavefront aberration from the refractive power with more ease and higher precision includes an optical system projecting slit light bundles onto a fundus of an examinee's eye and scanning the light bundles in predetermined first and second directions, an optical system with photodetectors placed in positions approximately conjugate with a cornea of the eye and placed in at least one meridian direction orthogonal to an optical axis of the photo-receiving optical system, and an arithmetic part obtaining, based on signals indicating phase differences from one of the photodetectors when photo-receiving the light bundles scanned in the first and second directions, refractive power in two directions at a corneal position corresponding to the photodetector position, and further obtains at least one of refractive power and a wavefront inclination by vector-synthesizing the obtained refractive power.

13 Claims, 11 Drawing Sheets

OPHTHALMIC MEASUREMENT APPARATUS

BACKGROUND OF THE INVENTION

1. Field of the Invention

The present invention relates to an ophthalmic measurement apparatus for measuring at least one of refractive power and wavefront aberration of an examinee's eye.

2. Description of Related Art

Conventionally, there is known an eye refractive power measurement apparatus for obtaining refractive power of an examinee's eye which varies in a meridian direction based on signals indicating phase differences from a plurality of photo detectors placed in the meridian direction (for example, see U.S. Pat. No. 5,907,388 corresponding to Japanese Patent Application Unexamined Publication No. Hei10-108837). In addition, there is known a wavefront aberration measurement apparatus for obtaining wavefront aberration of an examinee's eye using a Hartmann-Shack wavefront sensor (for example, see WO 99/27334 corresponding to Published Japanese Translation of PCT International Publication for Patent Application No. 2001-524662).

The wavefront aberration is obtained from the refractive power with ease and high precision if refractive power containing a skew ray component which is ordinarily present in the human eye is obtained.

SUMMARY OF THE INVENTION

An object of the invention is, in view of the above background arts, to provide an ophthalmic measurement apparatus capable of obtaining refractive power containing a skew ray component, and further, obtaining wavefront aberration from the refractive power with more ease and higher precision.

To achieve the objects and in accordance with the purpose of the present invention, an ophthalmic measurement apparatus includes a projection optical system which projects slit light bundles onto a fundus of an examinee's eye and scans the slit light bundles in predetermined first and second directions, a photo-receiving optical system provided with a plurality of photodetectors placed in positions approximately conjugate with a cornea of the examinee's eye and placed in at least one meridian direction orthogonal to an optical axis of the photo-receiving optical system, and an arithmetic part which obtains, based on a signal indicating a phase difference at the time when one of the photodetectors photo-receives the slit light bundle scanned in the first scanning direction and a signal indicating a phase difference at the time when the photodetector photo-receives the slit light bundle scanned in the second scanning direction, refractive power in two directions at a corneal position corresponding to a position of the photodetector, and further obtains at least one of refractive power and a wavefront inclination by vector-synthesizing the obtained refractive power in the two directions.

In another aspect of the present invention, an ophthalmic measurement apparatus includes a projection optical system which projects a slit light bundle onto a fundus of an examinee's eye and scans the slit light bundle in a predetermined direction, a photo-receiving optical system provided with a plurality of photodetectors which are placed in positions approximately conjugate with a cornea of the examinee's eye and placed in a first meridian direction orthogonal to an optical axis of the photo-receiving optical system and in a second meridian direction orthogonal to the optical axis of the photo-receiving optical system and intersecting with the first meridian direction at a predetermined angle, a rotation unit which rotates the scanning direction of the slit light bundle about an optical axis of the projection optical system and the photodetectors placed in the first and second meridian directions about the optical axis of the photo-receiving optical system in synchronization with each other, and an arithmetic part which obtains, based on a signal indicating a phase difference at the time when one of the photodetectors placed in the first meridian direction photo-receives the slit light bundle and a signal indicating a phase difference at the time when one of the photodetectors placed in the second meridian direction photo-receives the slit light bundle after being rotated by a predetermined angle, the photodetector being at the same distance from the optical axis of the photo-receiving optical system as the photodetector placed in the first meridian direction, refractive power in two directions at corneal positions corresponding to positions of the photodetectors, and further obtains at least one of refractive power and wavefront inclinations by vector-synthesizing the obtained refractive power in the two directions.

Additional objects and advantages of the invention are set forth in the description which follows, are obvious from the description, or may be learned by practicing the invention. The objects and advantages of the invention may be realized and attained by the ophthalmic measurement apparatus in the claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

A detailed description of preferred embodiments of an ophthalmic measurement apparatus embodied by the present invention is provided below with reference to the accompanying drawings.

First Preferred Embodiment

Figure 1:
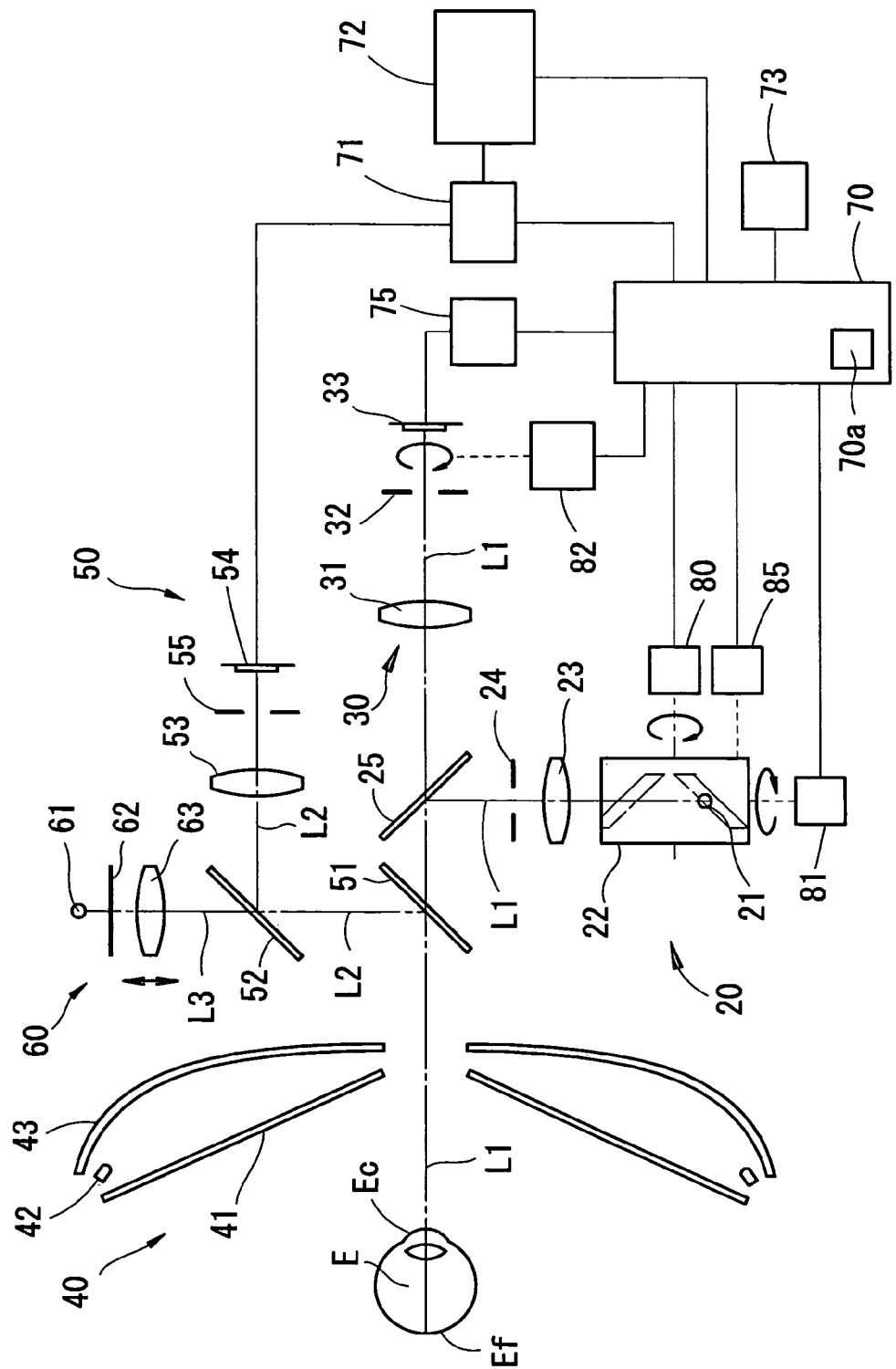
FIG. 1 shows a schematic configuration of an optical system and a control system of an ophthalmic measurement apparatus consistent with the first preferred embodiment of the present invention.

FIG. 1 shows a schematic configuration of an optical system and a control system of an ophthalmic measurement apparatus consistent with the first preferred embodiment of the present invention. The optical system includes an eye refractive power measurement optical system, a corneal shape measurement optical system, and a fixation target presenting optical system.

Figure 2:
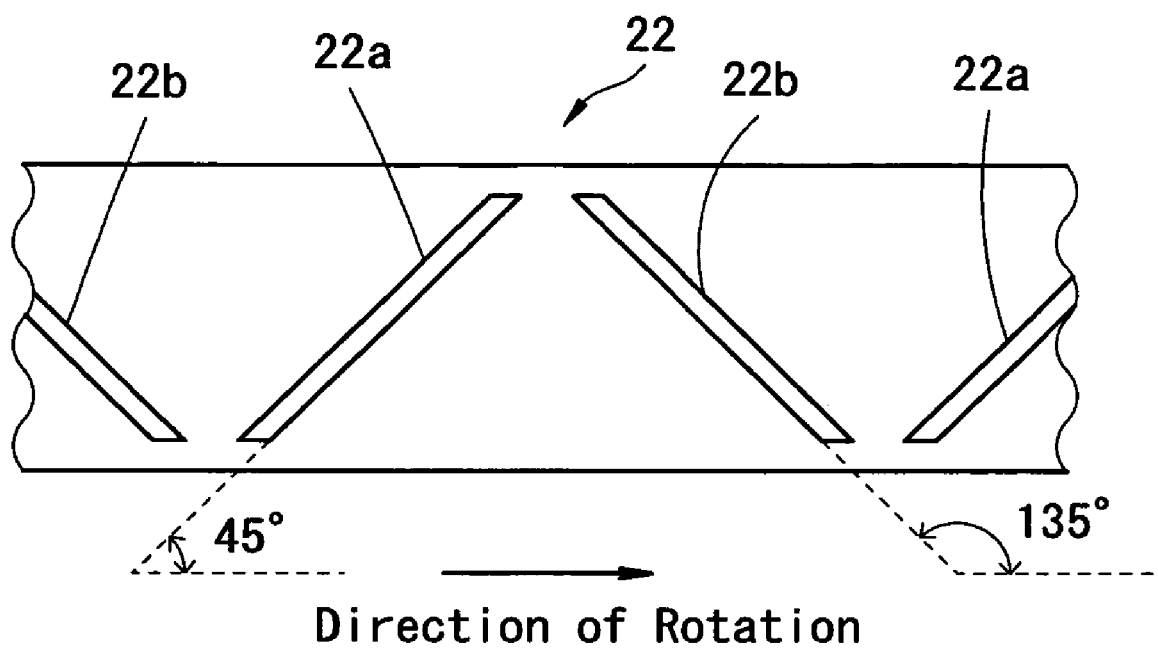
FIG. 2 is a view showing slits formed in a rotation sector consistent with the first preferred embodiment.

The eye refractive power measurement optical system includes a slit light bundle projection optical system 20 and a photo-receiving optical system 30. The projection optical system 20 includes an infrared light source 21 for measurement, a rotation sector 22 in which slits 22a and slits 22b orthogonal to each other are formed in a staggered configuration as shown in FIG. 2, a lens 23, a diaphragm 24, and a half mirror 25. Then, by rotation of the rotation sector 22, slit light bundles in two directions orthogonal to each other are alternately projected onto and scanned on a fundus Ef of an examinee's eye E. The rotation sector 22 is rotated by a rotation mechanism 80 such as a motor.

Figure 3:
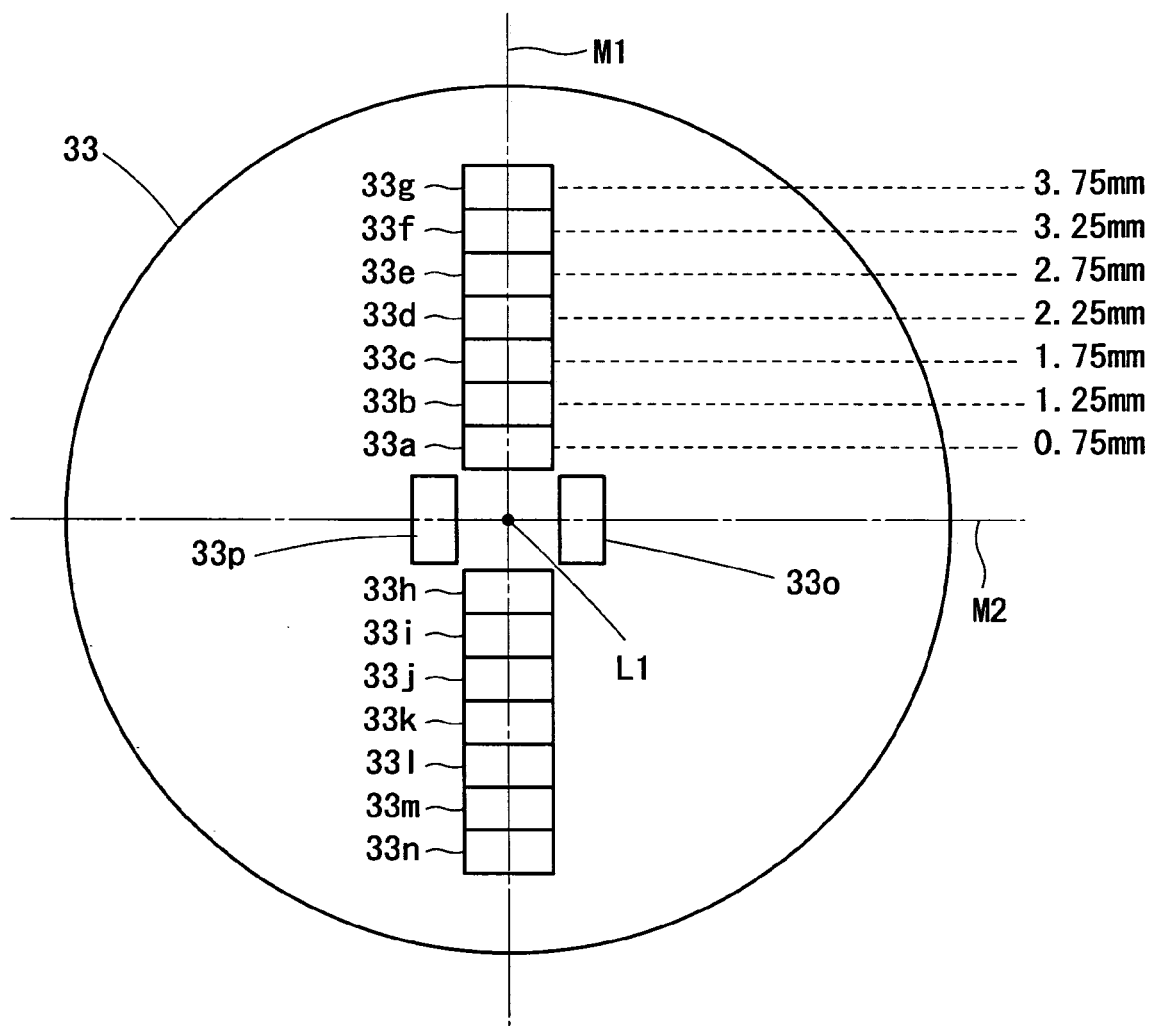
FIG. 3 is a view showing placement of photodetectors provided to a photo-receiving part consistent with the first preferred embodiment.

The photo-receiving optical system 30 includes a half mirror 25, a lens 31, a diaphragm 32 and a photo-receiving part 33. The photo-receiving part 33 is, as shown in FIG. 3, provided with sixteen photodetectors 33a to 33p placed in positions approximately conjugate with a cornea Ec of the eye E. Among them, the photodetectors 33a to 33n are placed in a first photo-receiving meridian M1 direction orthogonal to an optical axis L1 of the eye refractive power measurement optical system (the projection optical system 20 and the photo-receiving optical system 30), so that refractive power at different positions (sections) in a meridian direction of the cornea Ec is to be obtained. The photodetectors 33a to 33g consistent with the present embodiment are placed with intervals of 0.5 mm, starting from a position 0.75 mm apart from the optical axis L1, in an equivalent distance on the cornea Ec. The photodetectors 33h to 33n are respectively placed to be symmetrical to the photodetectors 33a to 33g with respect to the optical axis L1 (having the optical axis L1 in the middle). Besides, it is not always necessary for the photodetectors placed in the first photo-receiving meridian M1 direction to be symmetric with respect to the optical axis L1. On the other hand, the photodetectors 33o and 33p, which are used for detecting an optical axis position, are placed in a second photo-receiving meridian M2 direction which is different from the first photo-receiving meridian M1 direction (in the present embodiment, the second photo-receiving meridian M2 direction is orthogonal to the first photo-receiving meridian M1 direction), and arranged symmetrically with respect to the optical axis L1.

The rotation sector 22 and the photo-receiving part 33 are rotated about the optical axis L1 in synchronization with each other respectively by a rotation mechanism 81 such as a motor and a rotation mechanism 82 such as a motor. In the present embodiment, a first scanning direction of the slit light bundle formed by the slits 22a is set to correspond to (to be the same as) the first photo-receiving meridian M1 direction in which the photodetectors 33a to 33n are placed, and a second scanning direction of the slit light bundle formed by the slits 22b is set to correspond to (to be the same as) a direction orthogonal to the first photo-receiving meridian M1 direction. Besides, it is not necessary for the first scanning direction of the slit light bundle to correspond to the direction in which the photodetectors 33a to 33n are placed, and it is essential for the directions to have a known relationship. In addition, it is not necessary for the second scanning direction of the slit light bundle to be orthogonal to the first scanning direction, and it is essential for the directions to have a known relationship. A sensor 85 detects which is being scanned, the slit light bundle in the first scanning direction formed by the slits 22a or the slit light bundle in the second scanning direction formed by the slits 22b. A detection signal from the sensor 85 is inputted into an arithmetic control part 70.

Respective outputs from the photodetectors 33a to 33p are inputted into a phase-difference detection circuit 75. The phase-difference detection circuit 75 is connected to the arithmetic control part 70, and the rotation mechanisms 80, 81 and 82 are connected to and controlled by the arithmetic control part 70.

The corneal shape measurement optical system includes a placido-ring image projection optical system 40 and an image-pickup optical system 50. The projection optical system 40 includes a placido plate 41 where a number of ring-shaped targets are formed, near infrared light sources 42 for measurement which illuminate the placido plate 41 from behind, and a reflecting plate 43. The image-pickup optical system 50 includes a dichroic mirror 51 arranged on the optical axis L1 which reflects visible to near infrared light and transmits infrared light, a dichroic mirror 52 arranged on an optical axis L2 of the corneal shape measurement optical system (the image-pickup optical system 50) made coaxial with the optical axis L1, which transmits the visible light and reflects the near infrared light, a lens 53, a diaphragm 55, and a CCD camera 54 being image-pickup means. The image-pickup optical system 50 doubles as an observation optical system for an anterior segment of the eye E. The CCD camera 54 is connected to an image processing part 71 having an image memory, and the image processing part 71 is connected to a display 72 and the arithmetic control part 70. Besides, description on the constitution of the corneal shape measurement optical system and the measurement method thereof, having little relation with the present invention, is omitted (see, for example, U.S. Pat. No. 5,907,388 corresponding to Japanese Patent Application Unexamined Publication No. Hei10-8837). An input part 73 has various switches for inputting a command signal into the arithmetic control part 70.

A fixation target presenting optical system 60 includes a visible light source 61, a fixation target 62, and a lens 63 which is movable in a direction of an optical axis L3 of the fixation target presenting optical system made coaxial with the optical axis L2. At the time of eye refractive power measurement, the lens 63 is moved in the optical axis L3 direction to fog the eye E.

Incidentally, the light source 21 for measurement in the projection optical system 20 doubles as a light source for alignment, and a reflex formed at the center on the cornea Ec by the light source 21 is used as an alignment target in up/down and right/left directions. An examiner observes an image of the anterior-segment of the eye E displayed on the display 72 and performs alignment of the optical axis L1 of the eye refractive power measurement optical system with respect to the center on the cornea Ec so that the alignment target formed by the light source 21 and an unillusrated reticle have a predetermined relationship. Though alignment in a working distance direction (back/forth direction) can be performed in such a manner that the corneal reflex by the light source 21 is brought into focus, it is preferable to provide a separate alignment system. When the alignment is completed, eye refractive power and a corneal shape are measured by pushing a measurement switch (or automatically). Besides, while the alignment of the optical axis L1 of the eye refractive power measurement optical system is performed with respect to the corneal center in the present embodiment, it may be performed with respect to a visual axis. In this case, a fixation target presenting optical system disclosed in, for example, US Patent Application Publication No. 2003/0163122 corresponding to Japanese Patent Application Unexamined Publication No. 2003-245300 may be employed.

In eye refractive power measurement, the slit light bundle in the first scanning direction and the slit light bundle in the second scanning direction are alternately scanned on the fundus Ef, and reflection light bundles thereof are photo-received on the photodetectors 33a to 33p. The arithmetic control part 70 obtains refractive power and wavefront aberration at respective corneal positions corresponding to positions of the respective photodetectors based on signals indicating phase differences from the respective photodetectors.

Figure 4:
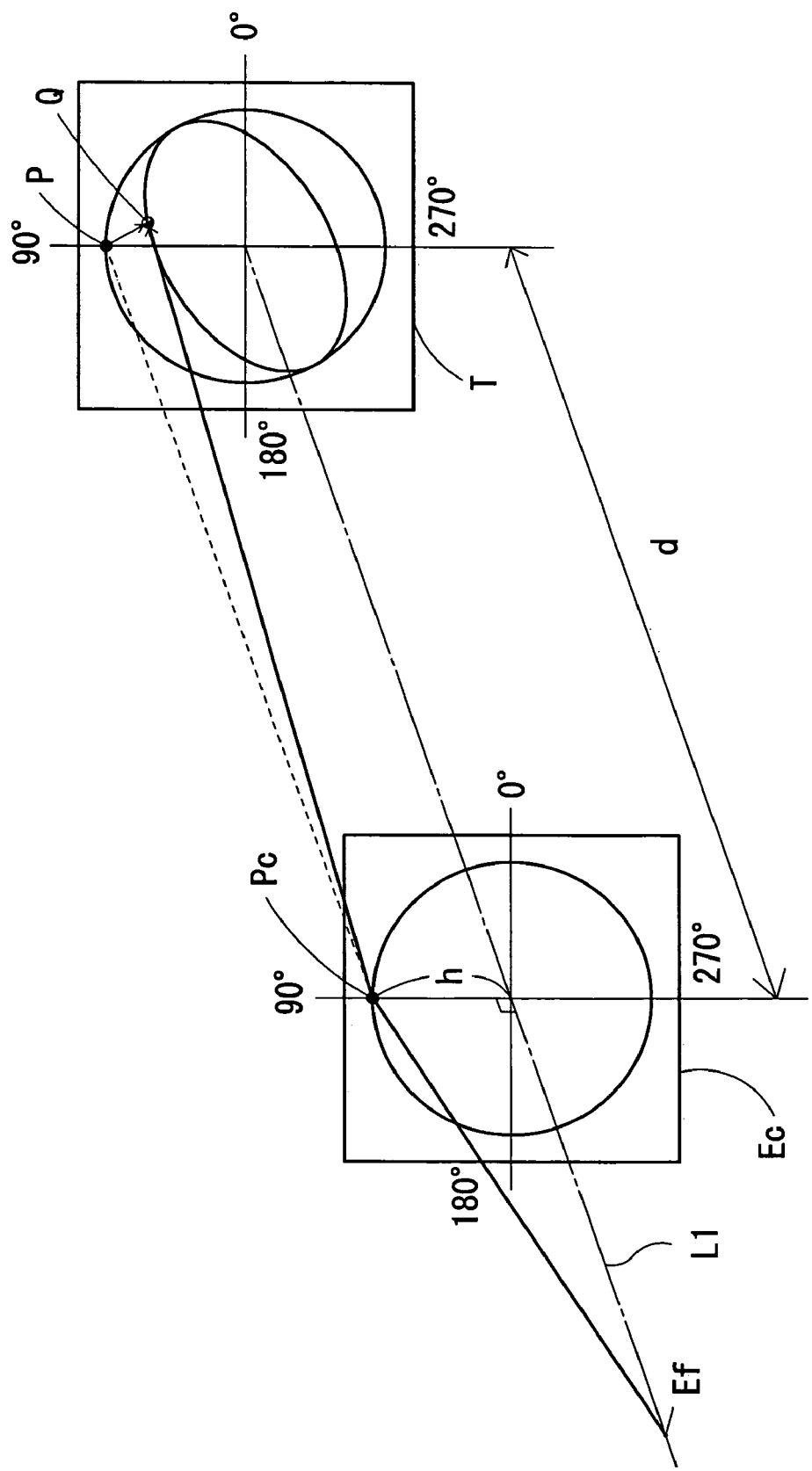
FIG. 4 is a view illustrating deviation of a ray which is caused by refractive power at a corneal position from which the ray reflected from a fundus exits.
Figure 5:
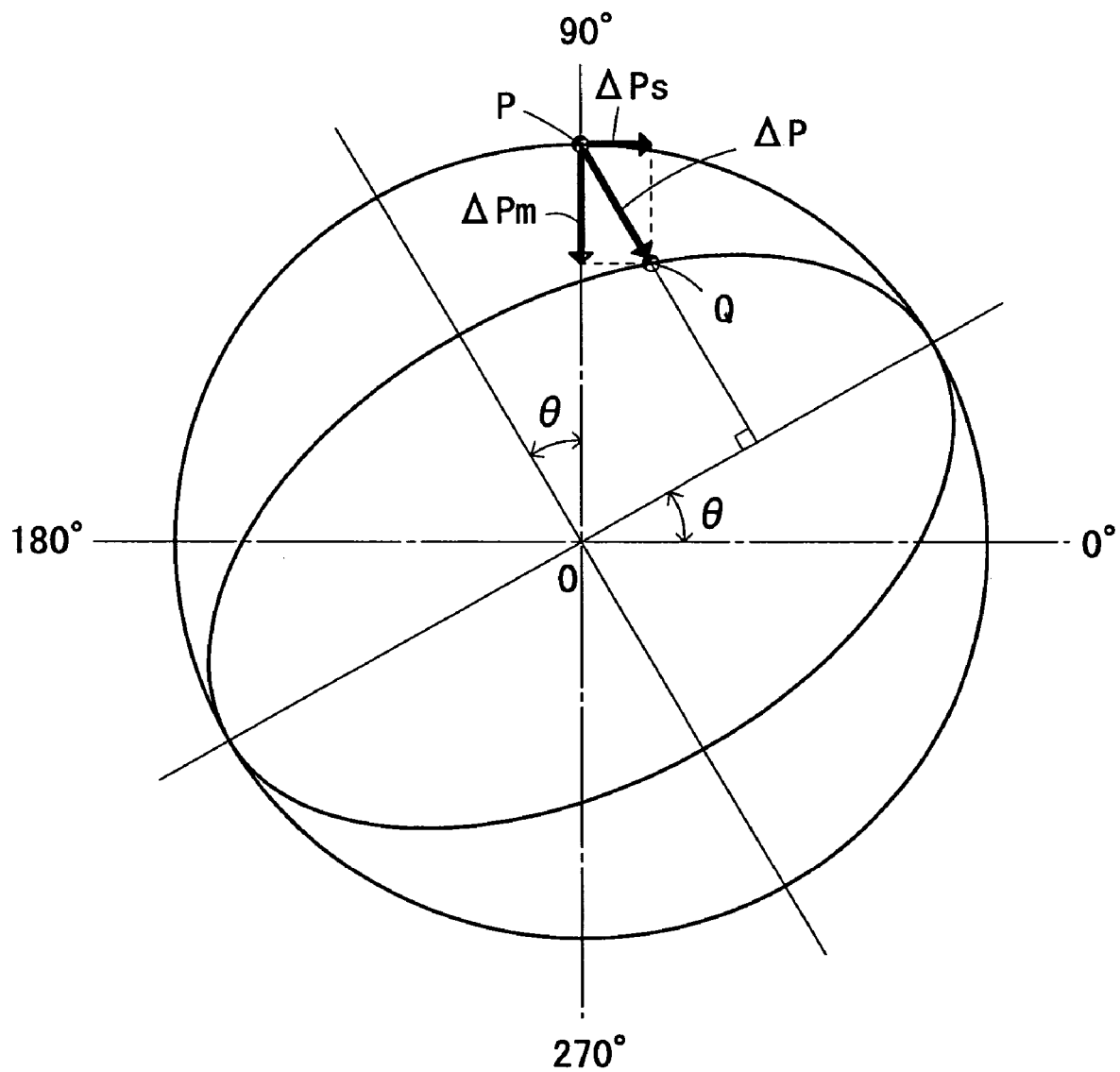
FIG. 5 is a view illustrating eye refractive power measurement consistent with the first preferred embodiment.

Hereinafter, a description will be given to measurement of the eye refractive power and calculation of the wavefront aberration. Now, assuming a polar coordinate system in which a horizontal direction is taken as a 0°-180° direction as shown in FIGS. 4 and 5, a case is considered where a ray, which starts from a fovea of the fundus Ef and exits from a point Pc on the cornea Ec, the point Pc being at a height h from the optical axis L1 in a 90°-270° direction, is deviated by refractive power at the corneal position. In the case of a non-aberration eye with no refractive error, the ray exiting from the point Pc travels in a straight line, so that a position of a point P (a corresponding point to the point Pc) on a screen T which includes a coordinate system perpendicular to the optical axis L1 and is placed at a certain distance d from the cornea Ec does not change. FIG. 5 shows the coordinate system on the screen T. In the case of an eye only with spherical error, the point P on the screen T of the ray exiting from the point Pc is deviated according to its spherical error in a meridian direction (meridional direction) which passes through an origin point O of the coordinate system, the origin point O positioned at the optical axis L1. In the case of an eye with refractive error containing astigmatism, in which a skew ray component is present, the ray exiting from the point Pc travels in a different direction from the meridian direction. In order to simplify the description, FIG. 5 shows a case where an eye E has only refractive power of regular astigmatism with a principal meridian angle θ and the ray exiting from the point Pc is deviated from the point P to a point Q on the screen T. In FIG. 5, refractive power ΔP which deviates the ray from the point P to the point Q is refractive power obtained by vector-synthesizing refractive power ΔPm in the meridian direction (meridional direction) being the 90°-270° direction and refractive power ΔPs in a direction orthogonal to the meridian direction (i.e., in a sagittal direction). Accordingly, once the refractive power in these two directions is obtained, refractive power containing (considering) the skew ray component and a wavefront inclination can be obtained at respective corneal positions.

Next, description on a method for obtaining the refractive power containing the skew ray component based on signals indicating phase differences from the respective photodetectors will be given. The arithmetic control part 70 controls to detect a position of the optical axis L1 in the first photo-receiving meridian M1 direction in which the photodetectors 33a to 33g are placed based on a signal indicating phase difference between the photodetectors 33o and 33p, and based on signals indicating phase differences between the optical axis L1 position and respective positions of the photodetectors in the first photo-receiving meridian M1 direction, refractive power at corneal positions corresponding to the respective positions of the photodetectors is obtained. Here, in order to simplify the description, the photodetector 33d in the first photo-receiving meridian M1 direction is explained as an example.

Figure 6:
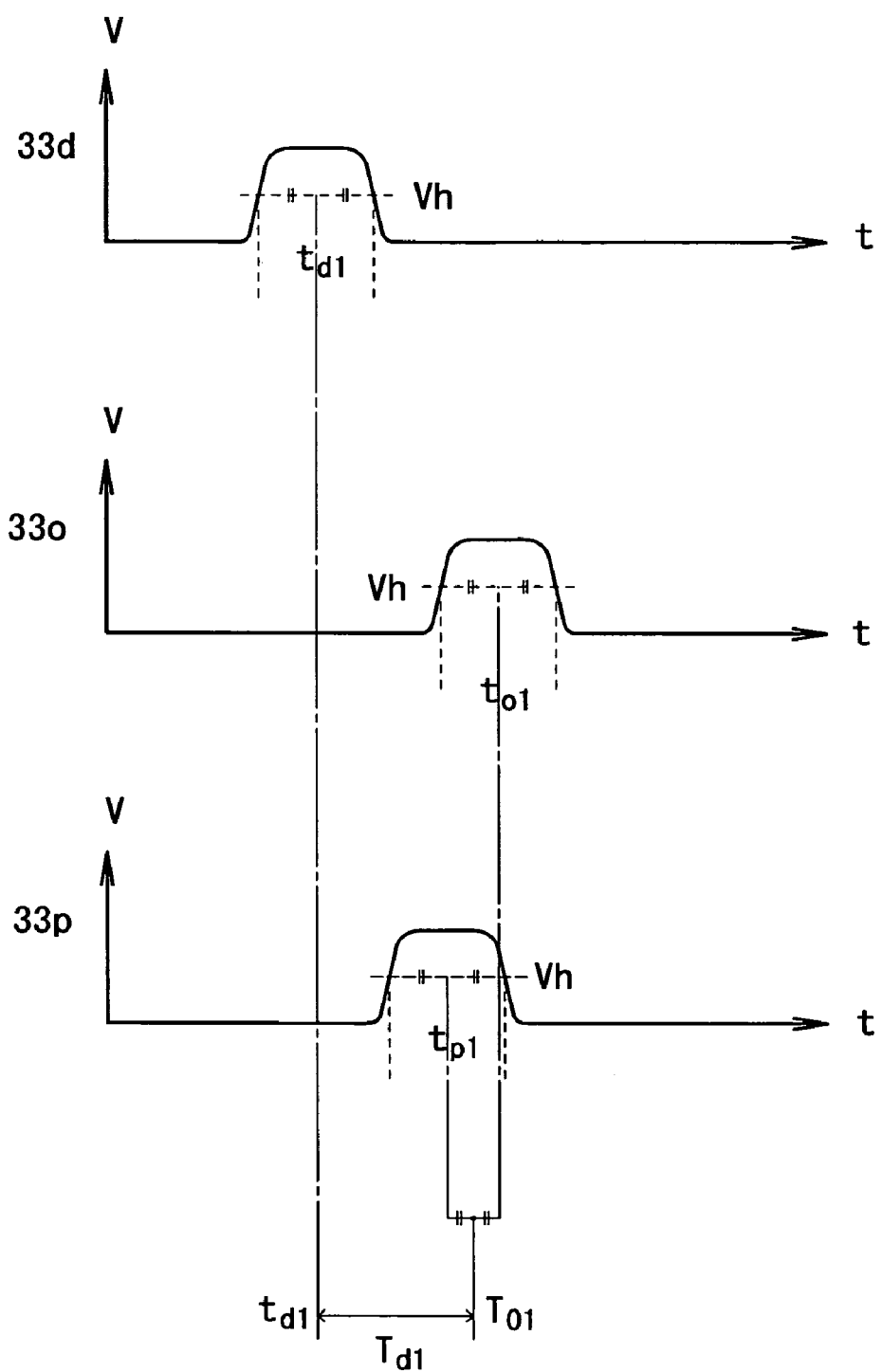
FIG. 6 is a view showing output signals from photodetectors at the time of photo-receiving a slit light bundle in a first scanning direction.

In a case where the eye E is with regular astigmatism, when the slit light bundle is scanned in the first scanning direction corresponding to (being the same as) the first photo-receiving meridian M1 direction, the slit light bundle reflected from the fundus Ef is photo-received on the respective photodetectors while inclined at the principal meridian angle θ of the astigmatism. Output signals from the respective photodetectors at this time are assumed to be as shown in FIG. 6 (here, the output signals from the photodetectors 33d, 33o and 33p are shown, and a signal level is indicated with V and time is indicated with t). The output signals from the respective photodetectors are shaped in a rectangular waveform and binarized at a predetermined threshold level Vh, and the halfway point of the rectaungular waveform is regarded as a phase signal of the photodetector. The phase signal of the photodetector 33d is detected as td1, the phase signal of the photodetector 33o is detected as to1, and the phase signal of the photodetector 33p is detected as tp1. A center phase signal T01 of the photodetectors 33o and 33p which are placed in a direction orthogonal to the first photo-receiving meridian M1 direction is the midpoint between the phase signals to1 and tp1. The phase signal T01 is regarded as the phase signal at the optical axis L1, so that a phase difference Td1 between the photodetector 33d and the optical axis L1 when the photodetector 33d photo-receives the slit light bundle in the first scanning direction is obtained by an expression, $$Td1 = T01 - td1.$$

Based on this phase difference Td1, the refractive power ΔPm in the first photo-receiving meridian M1 direction (first refractive power) with respect to the optical axis L1 position at a corneal position corresponding to the position of the photodetector 33d is obtained.

Figure 7:
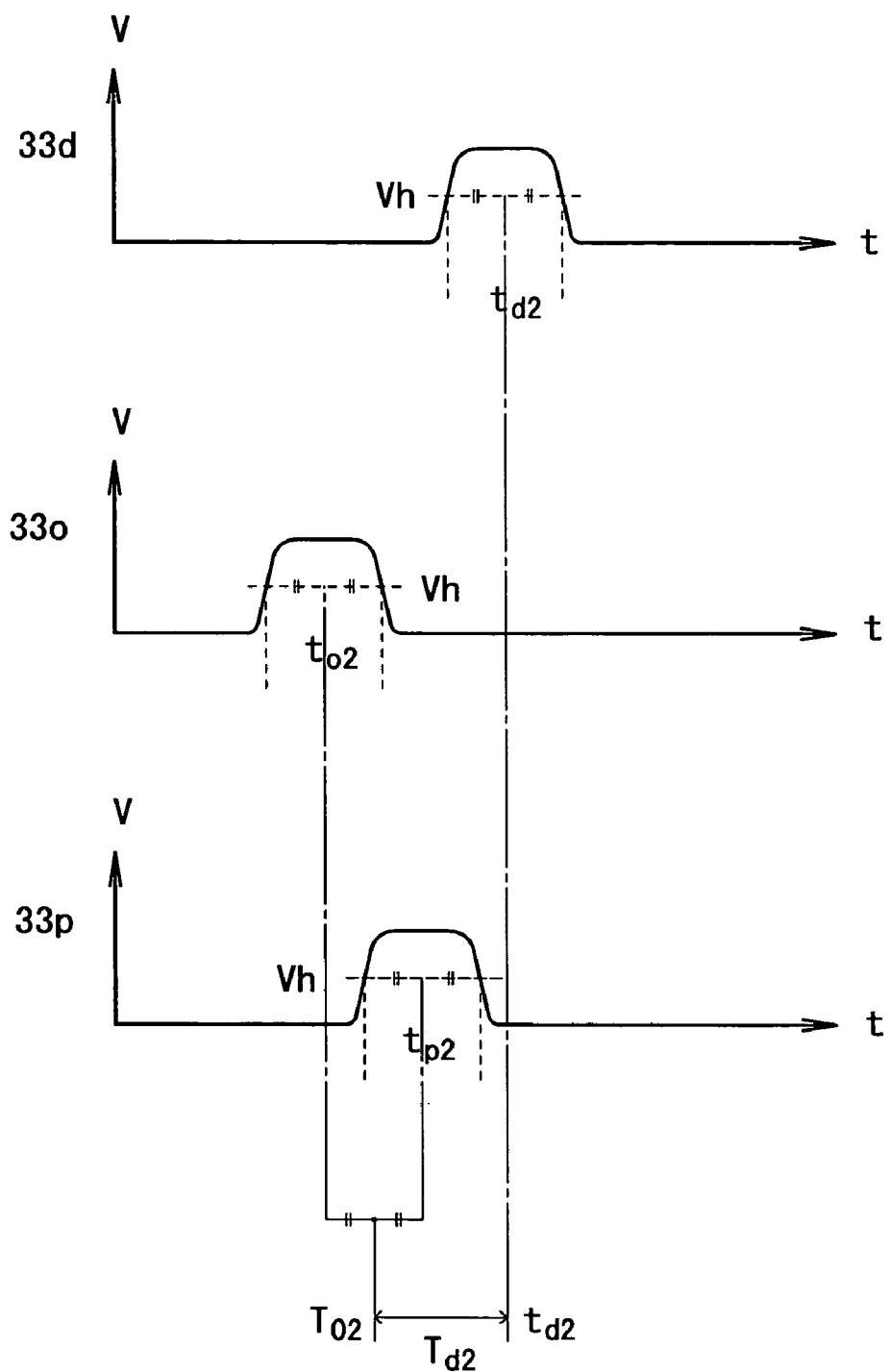
FIG. 7 is a view showing output signals from the photodetectors at the time of photo-receiving a slit light bundle in a second scanning direction.

Next, when the slit light bundle is scanned in the second scanning direction orthogonal to the first scanning direction, the slit light bundle reflected from the fundus Ef is photo-received on the respective photodetectors while inclined at the principal meridian angle θ of the astigmatism. Output signals from the respective photodetectors at this time are assumed to be as shown in FIG. 7 (here too, the output signals from the photodetectors 33d, 33o and 33p are shown, and a signal level is indicated with V and time is indicated with t). The phase signal of the photodetector 33d is detected as td2, the phase signal of the photodetector 33o is detected as to2, and the phase signal of the photodetector 33p is detected as tp2. A center phase signal T02 of the photodetectors 33o and 33p which are placed in the direction orthogonal to the first photo-receiving meridian M1 direction is the midpoint between the phase signals to2 and tp2. The phase signal T02 is also regarded as the phase signal at the optical axis L1, so that a phase difference Td2 between the photodetector 33d and the optical axis L1 when the photodetector 33d photo-receives the slit light bundle in the second scanning direction is obtained by an expression, Td2=td2-T02.

Based on this phase difference Td2, the refractive power ΔPs in the direction orthogonal to the first photo-receiving meridian M1 direction (second refractive power) with respect to the optical axis L1 position at the corneal position corresponding to the position of the photodetector 33d is obtained.

Once the refractive power ΔPm and the refractive power ΔPs in the two directions are obtained, the refractive power ΔP obtained by vector-synthesizing the refractive power ΔPm and the refractive power ΔPs can be obtained by an expression, ΔP={(ΔPs)2+(ΔPm)2}½.

As described above, when the slit light bundle is scanned in the first scanning direction, the optical axis L1 position in the first photo-receiving meridian M1 direction is detected by the photodetectors 33o and 33p placed in a direction different from the first photo-receiving meridian M1 direction, and based on the signals indicating the phase differences between the optical axis L1 position and the respective positions of the photodetectors in the first photo-receiving meridian M1 direction, the refractive power at the corneal positions corresponding to the respective positions of the photodetectors (i.e., the refractive power in the first photo-receiving meridian M1 direction) is obtained. In addition, also when the slit light bundle is scanned in the second scanning direction, the optical axis L1 position in the first photo-receiving meridian M1 direction is detected by the photodetectors 33o and 33p, and based on the signals indicating the phase differences between the optical axis L1 position and the respective positions of the photodetectors in the first photo-receiving meridian M1 direction, the refractive power at the corneal positions corresponding to the respective positions of the photodetectors (i.e., the refractive power in the direction orthogonal to the first photo-receiving meridian M1 direction) is obtained.

Once the refractive power in one corneal meridian direction is obtained, the rotation sector 22 and the photo-receiving part 33 are rotated respectively by the rotation mechanism 81 and the rotation mechanism 82 in synchronization with each other about the optical axis L1 by 180° in increments of a predetermined angle (e.g., one degree) to obtain refractive power in a meridian direction at respective rotation angles. By doing this, refractive power and traveling directions of the rays containing the skew ray components at a plurality of corneal positions in all meridian directions in increments of the predetermined angle are obtained. A measurement result obtained at this time may be displayed in a form of a map and the like on the display 72.

As the refractive power in the two directions at the respective corneal positions is obtained as described above, and a resultant vector of the refractive power in the two directions indicates the traveling direction of the ray, a surface orthogonal to the traveling direction becomes a wavefront at the corneal position. In other words, based on the refractive power in the two directions at the respective corneal positions, wavefront inclinations at the respective corneal positions are obtained, which are obtained by a Hartmann-Shack wavefront sensor. By quoting a description on wavefront analysis by the Hartmann-Shack wavefront sensor, a wavefront W(X,Y) on an orthogonal coordinate system is expressed by the following expressions, $$\frac{\partial W(X,Y)}{\partial X} = \frac{\Delta x}{f}$$

$$\frac{\partial W(X,Y)}{\partial Y} = \frac{\Delta y}{f}.$$

In the expressions above, (X,Y) indicates coordinates on a pupil surface, f indicates a focal length of a lenslet array, and Δy/f and Δx/f indicate a wavefront inclination. Wavefront aberration can be obtained based on the wavefront inclination by determining a degree of an expansion coefficient using Zernike's polynomials as follows.

$$W(X,Y) = \sum_{i=0}^{n} \sum_{j=0}^{f} c_{ij} Z_{ij}(X,Y)$$

In the description on the present embodiment, a wavefront inclination at the point Pc on the cornea Ec at the height h from the optical axis L1 is expressed by the first refractive power ΔPm in the meridian direction and the second refractive power ΔPs in the direction orthogonal to the meridian direction on the polar coordinate system. Let αm represent a wavefront inclination in the meridian direction and αs represent a wavefront inclination in a direction orthogonal to the meridian direction, the respective wavefront inclinations αm and αs are obtained by the following expressions, tan αm=h·ΔPm tan αs=h·ΔPs.

A wavefront W(X,Y) maybe obtained by converting the wavefront inclinations αm and αs in the two directions on the polar coordinate system into an X-Y orthogonal coordinate system. Besides, it may be also obtained from a wavefront W(h,θ) on the polar coordinate system without conversion. The obtained wavefront aberration is displayed in a form of a map and the like on the display 72.

Second Preferred Embodiment

Figure 8:
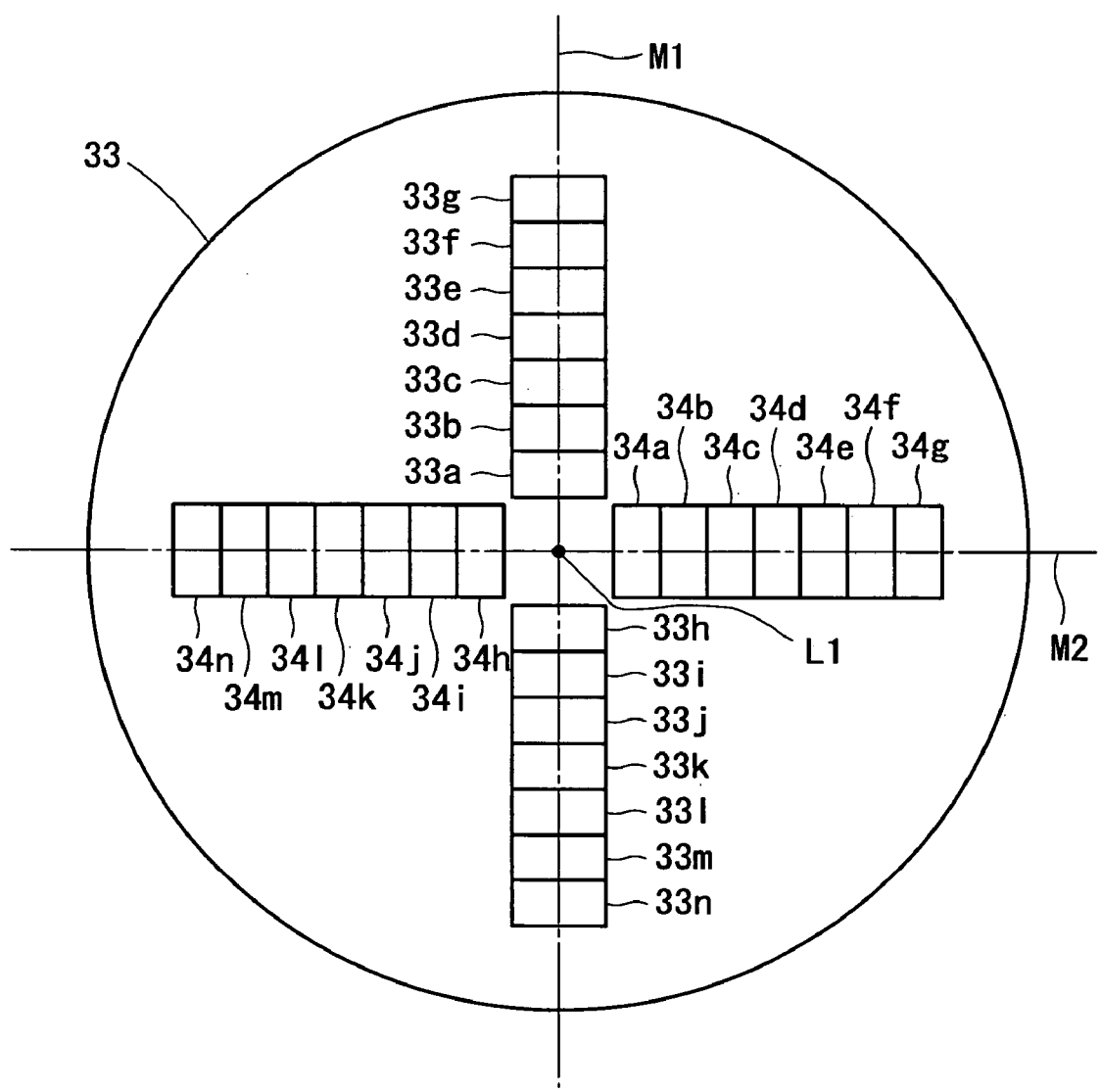
FIG. 8 is a view showing placement of photodetectors provided to a photo-receiving part consistent with the second preferred embodiment.

FIG. 8 is a view showing placement of photodetectors provided to a photo-receiving part 33 consistent with the second preferred embodiment. As the constitution of the other components is basically similar to the first embodiment, description thereon is omitted. Similarly to the first embodiment (FIG. 3), photodetectors 33a to 33n are placed in the first photo-receiving meridian M1 direction orthogonal to the optical axis L1. On the other hand, in the second photo-receiving meridian M2 direction orthogonal to the optical axis L1 and the first photo-receiving meridian M1 direction, photodetectors 34a to 34n are placed in positions in which the photodetectors 33a to 33n are located when rotated about the optical axis L1 by 90°. Scanning of slit light bundles is, similarly to the above-described embodiment, set so that a first scanning direction corresponds to (becomes the same as) the first photo-receiving meridian M1 direction, and a second scanning direction corresponds to (becomes the same as) the second photo-receiving meridian M2 direction.

In the placement of such photodetectors, a pair of the photodetectors 34a and 34h (or another pair of the photodetectors) in the second photo-receiving meridian M2 direction is regarded as photodetectors for detecting an optical axis position in the first photo-receiving meridian M1 direction, and a pair of the photodetectors 33a and 33h (or another pair of the photodetectors) in the first photo-receiving meridian M1 direction is regarded as photodetectors for detecting an optical axis position in the second photo-receiving meridian M2 direction.

Figure 9:
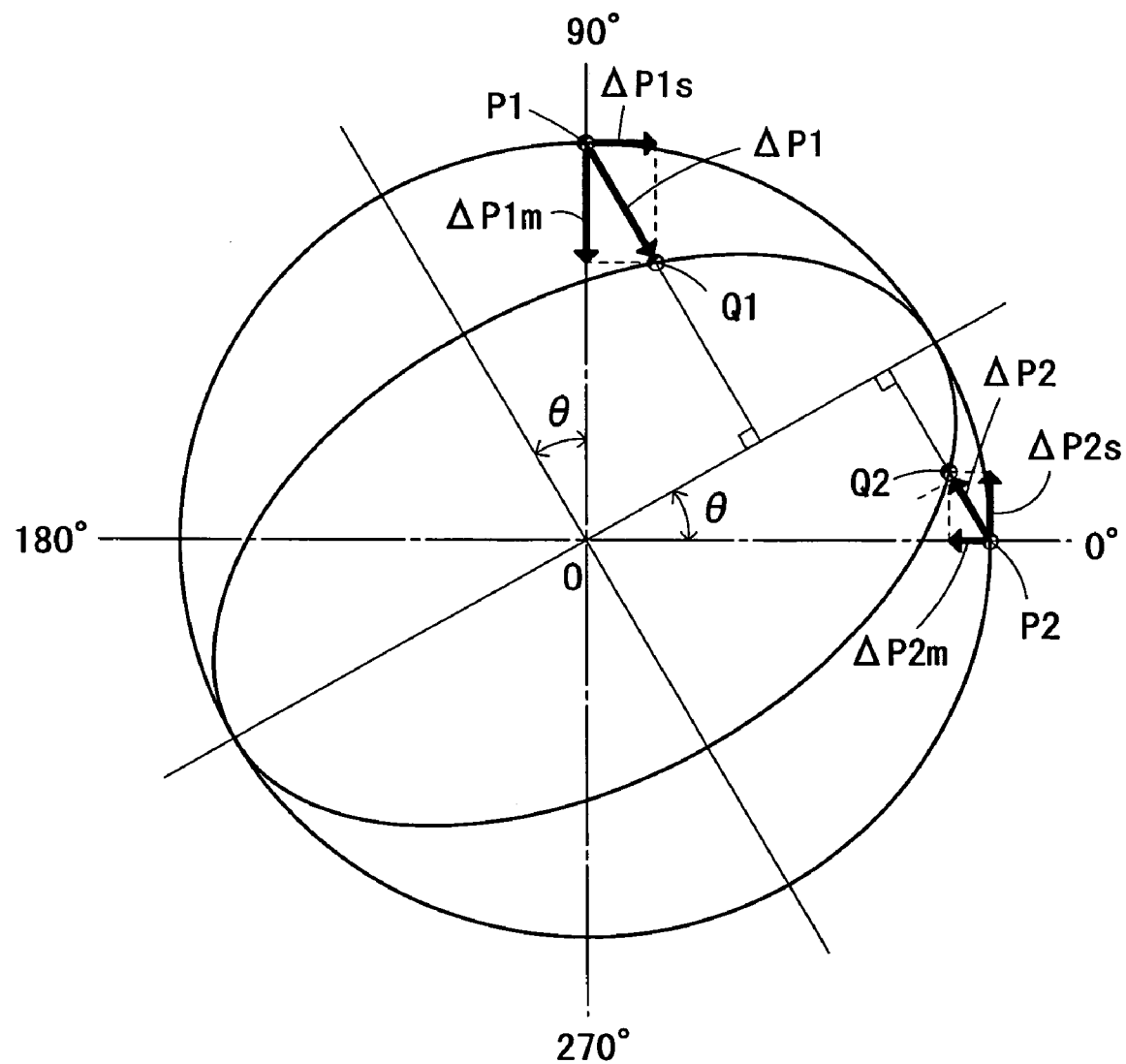
FIG. 9 is a view illustrating eye refractive power measurement consistent with the second preferred embodiment.

Eye refractive power measurement in the second embodiment will be described referring to FIG. 9. FIG. 9 has the same base as FIG. 5 while showing a case where a point P1 in a 90°-270° corneal meridian direction deviates to a point Q1, and a point P2 in a 0°-180° corneal meridian direction deviates to a point Q2.

Firstly, when the slit light bundle is scanned in the first scanning direction corresponding to the first photo-receiving meridian M1 direction which is placed in (corresponds to) the 90°-270° corneal meridian direction, a position of the optical axis L1 in the first photo-receiving meridian M1 direction is detected by the photodetectors 34a and 34h in the second photo-receiving meridian M2 direction, and based on signals indicating phase differences between the optical axis L1 position and respective positions of the photodetectors in the first photo-receiving meridian M1 direction, refractive power at corneal positions corresponding to the respective positions of the photodetectors (first refractive power in the 90°-270° corneal meridian direction) ($\Delta$P1m) is obtained. At the same time, a position of the optical axis L1 in a direction orthogonal to the second photo-receiving meridian M2 direction is detected by the photodetectors 33a and 33h in the first photo-receiving meridian M1 direction, and based on signals indicating phase differences between the optical axis L1 position and respective positions of the photodetectors in the second photo-receiving meridian M2 direction, refractive power at corneal positions corresponding to the respective positions of the photodetectors (second refractive power in a direction orthogonal to the 0°-180° corneal meridian direction) ($\Delta$P2s) is obtained. These measurement results are stored in a memory 70a provided to the arithmetic control part 70.

Next, when the slit light bundle is scanned in the second scanning direction corresponding to the second photo-receiving meridian M2 direction which is placed in (corresponds to) the 0°-180° corneal meridian direction, a position of the optical axis L1 in a direction orthogonal to the first photo-receiving meridian M1 direction is detected by the photodetectors 34a and 34h in the second photo-receiving meridian M2 direction, and based on signals indicating phase differences between the optical axis L1 position and the respective positions of the photodetectors in the first photo-receiving meridian M1 direction, refractive power at the corneal positions corresponding to the respective positions of the photodetectors (second refractive power in a direction orthogonal to the 90°-270° corneal meridian direction) ($\Delta$P1s) is obtained. At the same time, a position of the optical axis L1 in the second photo-receiving meridian M2 direction is detected by the photodetectors 33a and 33h in the first photo-receiving meridian M1 direction, and based on signals indicating phase differences between the optical axis L1 position and the respective positions of the photodetectors in the second photo-receiving meridian M2 direction, refractive power at the corneal positions corresponding to the respective positions of the photodetectors (first refractive power in the 0°-180° corneal meridian direction) ($\Delta$P2m) is obtained. These measurement results are also stored in the memory 70a provided to the arithmetic control part 70.

The arithmetic control part 70 calls up the measurement results by the slit light bundle in the first scanning direction and the measurement results by the slit light bundle in the second scanning direction from the memory 70a, and obtains refractive power obtained by vector-synthesizing the refractive power in the two directions at the corneal positions corresponding to the respective positions of the photodetectors in the first photo-receiving meridian M1 direction, and refractive power obtained by vector-synthesizing the refractive power in the two directions at the corneal positions corresponding to the respective positions of the photodetectors in the second photo-receiving meridian M2 direction. In other words, at the point P1 on the cornea, $\Delta$P1 is obtained by vector-synthesizing $\Delta$P1m and $\Delta$P1s, and at the point P2 on the cornea, $\Delta$P2 is obtained by vector-synthesizing $\Delta$P2m and $\Delta$P2s. In addition, similarly to the first embodiment, the arithmetic control 70 obtains wavefront inclinations based on the refractive power in the two directions at the respective corneal positions to obtain wavefront aberration.

In the present embodiment, in order to obtain refractive power in all corneal meridian directions in increments of a predetermined angle, it is essential only that the rotation sector 22 and the photo-receiving part 33 are rotated by 90° in increments of the predetermined angle, whereby a measurement time can be shortened compared with the first embodiment.

Third Preferred Embodiment

Figure 10A:
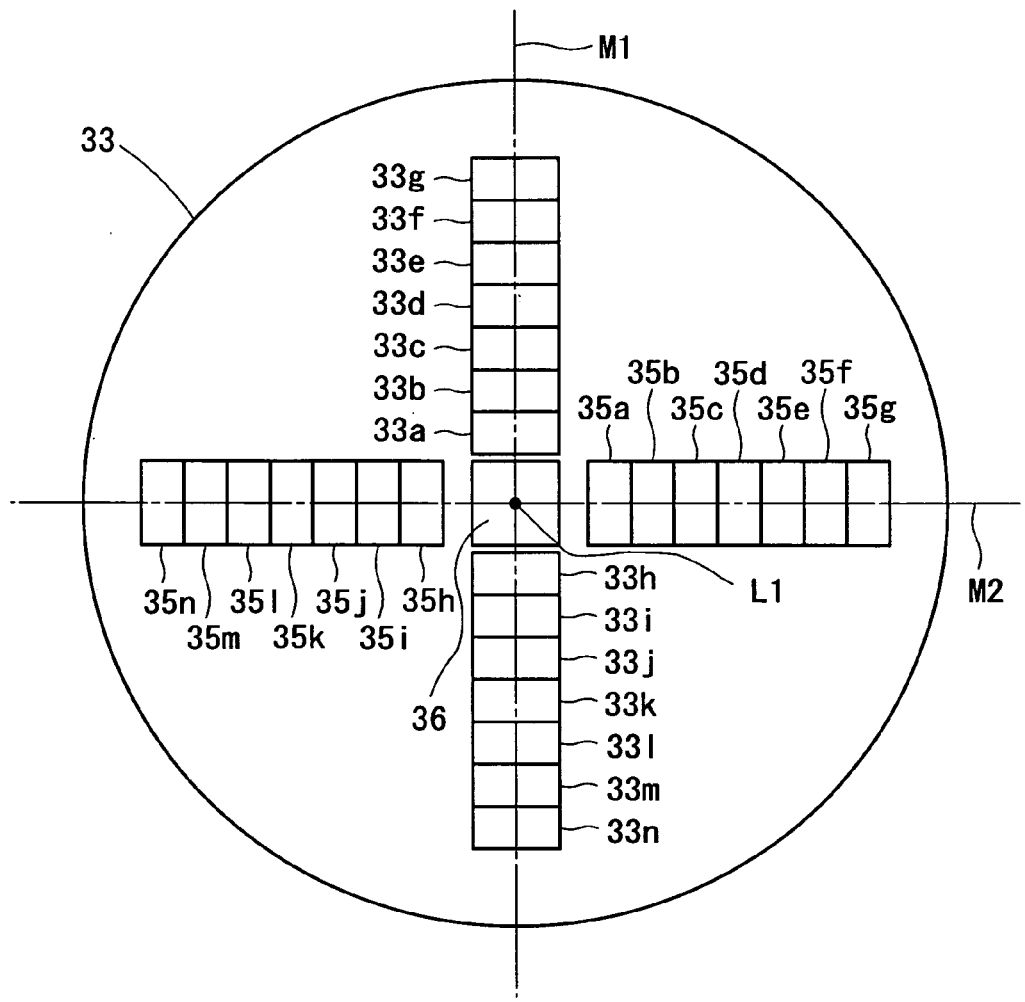
FIG. 10A is a view showing placement of photodetectors provided to a photo-receiving part consistent with the third preferred embodiment.

FIG. 10A is a view showing placement of photodetectors provided to a photo-receiving part 33 consistent with the third preferred embodiment. Photodetectors 35a to 35n in the second photo-receiving meridian M2 direction consistent with the third embodiment, of which placement is changed from that of the photodetectors 34a to 34n in the second photo-receiving meridian M2 direction consistent with the second embodiment, are placed with displacement so that respective distances thereof from the optical axis L1 become different from (do not correspond to) distances of photodetectors 33a to 33n in the first photo-receiving meridian M1 direction from the optical axis L1. In the third embodiment, the placement of the photodetectors in the second photo-receiving meridian M2 direction is displaced from that of the photodetectors in the first photo-receiving meridian M1 direction by 0.25 mm which is a half of 0.5 mm being a space between the photodetectors. Owing to such placement, when the respective photodetectors in the second photo-receiving meridian M2 direction are rotated by 90°, refractive power at corneal positions displaced from the corneal positions corresponding to the respective positions of the photodetectors in the first photo-receiving meridian M1 direction is obtained in the same corneal meridian direction. Besides, in the present third embodiment, similarly to the first embodiment, through the rotation of the rotation sector 22 and the photo-receiving part 33 by 180° in increments of a predetermined angle, refractive power in all corneal meridian directions in increments of the predetermined angle can be obtained.

As a method for improving measurement resolving power, it is essential only to increase the number of the photodetectors in the meridian directions; however, as areas of the photodetectors need to be secured considering an S/N ratio, there is a limit to the increase in number. According to the present third embodiment, the measurement resolving power can be improved while securing the areas of the respective photodetectors.

Figure 10B:
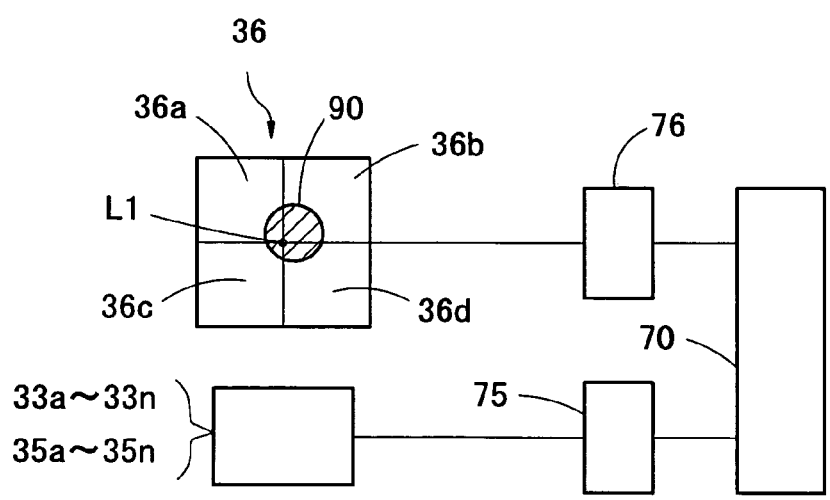
FIG. 10B shows a schematic configuration of a signal processing system of a four-split photodetector provided to the photo-receiving part consistent with the third preferred embodiment.

In addition, in the photo-receiving part 33 consistent with the present third embodiment, a four-split photodetector 36 for detecting an alignment state is placed in the middle of the photodetectors 33a, 33h, 35a and 35h. FIG. 10B shows a schematic configuration of a signal processing system of the photodetector 36. The photodetector 36 includes four photodetectors 36a to 36d having the optical axis L1 as their center. The photodetector 36 is connected to a detection circuit 76 separate from the phase-difference detection circuit 75 for the photodetectors 33a to 33n and 35a to 35n for measurement, and the detection circuit 76 is connected to the arithmetic control part 70. The light source 21 for measurement doubles as a light source for alignment and its corneal reflection light bundle is photo-received as a reflex 90 on the photodetector 36.

An alignment state of the eye refractive power measurement optical system in the up/down and right/left directions with respect to the eye E is detected from a balance between light amounts of the four photodetectors 36a to 36d. To be more specific, when the alignment state is appropriate, the reflex 90 on the photodetector 36 centers at the optical axis L1 and output signals from the photodetectors 36a to 36d become almost equal. When the alignment state shows deviation to the right, the reflex 90 is located in the right part on the photodetector 36 and the output signals from the photodetectors 36b and 36d become larger than those from the photodetectors 36a and 36c. When the alignment state shows deviation in an upward direction, the reflex 90 is located in the upper part on the photodetector 36 and the output signals from the photodetectors 36a and 36b become larger than those from the photodetectors 36c and 36d. Accordingly, a direction and a degree of alignment deviation can be detected. In addition, based on an output signal from the entire photodetector 36, a corneal reflection level can be detected.

In measuring the refractive power in all meridian directions by rotating the rotation sector 22 and the photo-receiving part 33, the arithmetic control part 70 controls to store the output signal from the photodetector 36 together with phase signals from the photodetectors 33a to 33n and 35a to 35n. Afterward, at the stage of obtaining the refractive power in the respective meridian directions, detection information from the photodetector 36 is utilized for judging usefulness of measurement data in the respective meridian directions. In a case where alignment deviation in one meridian direction exceeds a permissible range or a case where there is abnormality in coneal reflection, the measurement data in the meridian direction is subjected to interpolation by the measurement data in the neighboring meridian direction and the like. Besides, the alignment state may be detected using the CCD camera 54 being observation means for an anterior segment of an eye.

Fourth Preferred Embodiment

Figure 11:
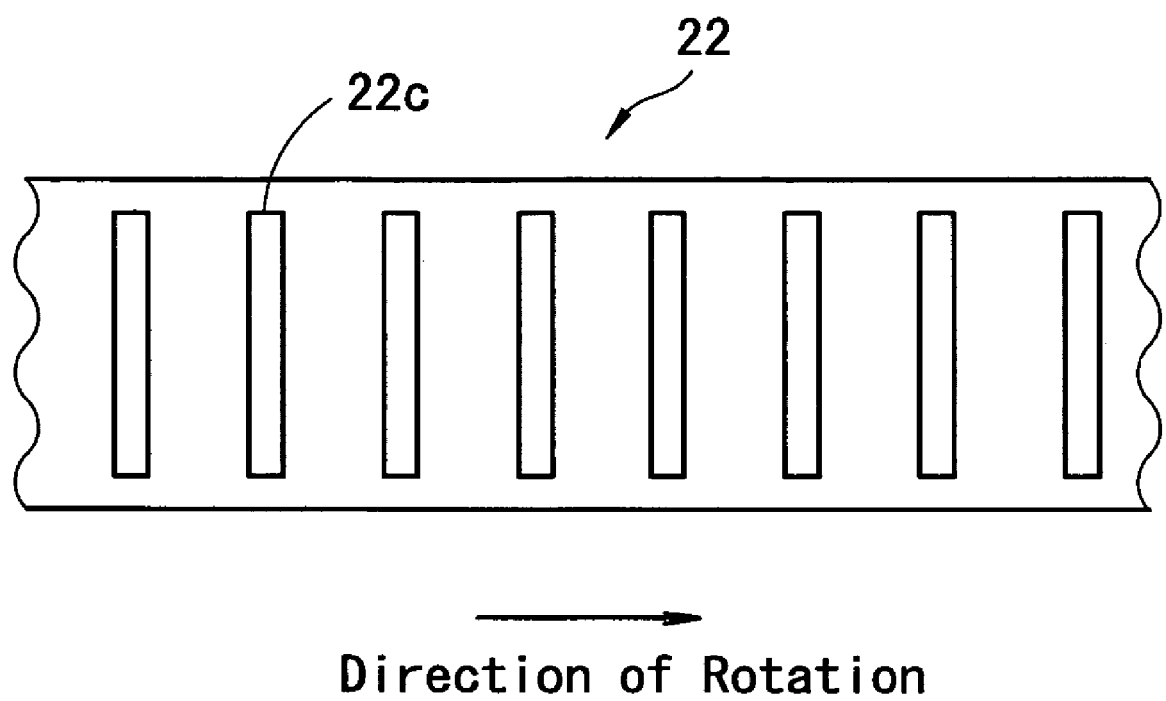
FIG. 11 is a view showing slits formed in a rotation sector consistent with the fourth preferred embodiment.

FIG. 11 is a view showing slits formed in a rotation sector 22 consistent with the fourth preferred embodiment. Placement of photodetectors provided to a photo-receiving part 33 consistent with the fourth preferred embodiment is configured, similarly to the second embodiment (FIG. 8), such that photodetectors 33a to 33n are placed in the first photo-receiving meridian M1 direction and photodetectors 34a to 34n are placed in the second photo-receiving meridian M2 direction orthogonal to the first photo-receiving meridian M1 direction.

As shown in FIG. 11, in the rotation sector 22 consistent with the fourth embodiment, only slits 22c in one direction are formed to scan only a slit light bundle in one scanning direction, and the scanning direction is set to correspond to (become the same as) the first photo-receiving meridian M1 direction in which the photodetectors 33a to 33n are placed, which is shown in FIG. 8.

Eye refractive power measurement in the fourth embodiment will be described referring to FIGS. 8 and 9 consistent with the second embodiment. Firstly, the slit light bundle is scanned in the scanning direction corresponding to the first photo-receiving meridian M1 direction which is placed in (corresponds to) the 90°-270° corneal meridian direction, and a position of the optical axis L1 in the first photo-receiving meridian M1 direction is detected by the photodetectors 34a and 34h in the second photo-receiving meridian M2 direction, and then based on signals indicating phase differences between the optical axis L1 position and respective positions of the photodetectors in the first photo-receiving meridian M1 direction, refractive power at corneal positions corresponding to the respective positions of the photodetectors (first refractive power in the 90°-270° corneal meridian direction) ($\Delta P1m$) is obtained. At the same time, a position of the optical axis L1 in a direction orthogonal to the second photo-receiving meridian M2 direction is detected by the photodetectors 33a and 33h in the first photo-receiving meridian M1 direction, and based on signals indicating phase differences between the optical axis L1 position and respective positions of the photodetectors in the second photo-receiving meridian M2 direction, refractive power at corneal positions corresponding to the respective positions of the photodetectors (second refractive power in the direction orthogonal to the 0°-180° corneal meridian direction)($\Delta P2s$) is obtained.

Next, the rotation sector 22 and the photo-receiving part 33 are rotated about the optical axis L1 by 90°. The slit light bundle is scanned in a scanning direction corresponding to the first photo-receiving meridian M1 direction which is placed in (corresponds to) the 0°-180° corneal meridian direction, and a position of the optical axis L1 in the second photo-receiving meridian M2 direction is detected by the photodetectors 33a and 33h in the first photo-receiving meridian M1 direction, and then based on signals indicating phase differences between the optical axis L1 position and the respective positions of the photodetectors in the second photo-receiving meridian M2 direction, refractive power at corneal positions corresponding to the respective positions of the photodetectors (second refractive power in the direction orthogonal to the 90°-270° corneal meridian direction) ($\Delta P1s$) is obtained. At the same time, a position of the optical axis L1 in the first photo-receiving meridian M1 direction is detected by the photodetectors 34a and 34h in the second photo-receiving meridian M2 direction, and based on signals indicating phase differences between the optical axis L1 position and the respective positions of the photodetectors in the first photo-receiving meridian M1 direction, refractive power at corneal positions corresponding to the respective positions of the photodetectors (first refractive power in the 0°-180° corneal meridian direction)($\Delta P2m$) is obtained.

In the present embodiment, it is essential to scan the slit light bundle only in one scanning direction, whereby a measurement time can be shortened compared with the first embodiment.

The first to fourth preferred embodiments described above may be variously modified within the scope of the same technical idea. For example, in addition to the mechanical rotation of the rotation sector 22 and the photo-receiving part 33 in the preferred embodiments, the rotation sector 22 and the photo-receiving part 33 may be rotated optically in synchronization with each other by placing an image rotator in an optical path common to the projection optical system 20 and the photo-receiving optical system 30. In addition, for a relationship between the scanning direction of the slit light bundle and the direction in which the photodetectors are placed, a relationship between the refractive power in the two directions which is to be vector-synthesized, and the like, well-known relationships may be employed, and they are not limited to the above described embodiments.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An ophthalmic measurement apparatus comprising:
   a projection optical system which projects slit light bundles onto a fundus of an examinee's eye, the projection optical system scanning the slit light bundles in predetermined first and second directions;
   a photo-receiving optical system provided with a plurality of photodetectors placed in positions approximately conjugate with a cornea of the examinee's eye, the photodetectors being placed in at least one meridian direction orthogonal to an optical axis of the photo-receiving optical system; and
   an arithmetic part which obtains, based on a signal indicating a phase difference at the time when one of the photodetectors photo-receives the slit light bundle scanned in the first scanning direction and a signal indicating a phase difference at the time when the photodetector photo-receives the slit light bundle scanned in the second scanning direction, refractive power in two directions at a corneal position corresponding to a position of the photodetector, and further obtains at least one of refractive power and a wavefront inclination by vector-synthesizing the obtained refractive power in the two directions.

2. The ophthalmic measurement apparatus according to claim 1, further comprising a rotation unit which rotates the first and the second scanning directions of the slit light bundles about an optical axis of the projection optical system, and the photodetectors placed in the meridian direction about the optical axis of the photo-receiving optical system, in synchronization with each other.

3. The ophthalmic measurement apparatus according to claim 1, wherein the arithmetic part obtains, based on a signal indicating a phase difference between a position of the optical axis of the photo-receiving optical system and the photodetector position, the refractive power in the two directions at the corneal position corresponding to the photodetector position.

4. The ophthalmic measurement apparatus according to claim 3, further comprising an optical-axis-deviation detection unit which detects deviation of the optical axis of the photo-receiving optical system with respect to one of a corneal center and a visual axis,
   wherein the arithmetic part judges whether the refractive power at the corneal position corresponding to the photodetector position is useful based on a detection result obtained by the optical-axis-deviation detection unit.

5. The ophthalmic measurement apparatus according to claim 1, wherein
   the first scanning direction corresponds to the meridian direction in which the photodetectors are placed, and
   the second scanning direction is orthogonal to the first scanning direction.

6. The ophthalmic measurement apparatus according to claim 1, wherein
   the photodetectors are placed in two meridian directions orthogonal to the optical axis of the photo-receiving optical system, and
   the first and second scanning directions correspond to the two meridian directions in which the photodetectors are placed.

7. The ophthalmic measurement apparatus according to claim 6, wherein the photodetectors placed in the first meridian direction and the photodetectors placed in the second meridian direction are different in distance from the optical axis of the photo-receiving optical system.

8. The ophthalmic measurement apparatus according to claim 1, further comprising a corneal-reflection detection unit which detects corneal reflection of the slit light bundles,
   wherein the arithmetic part judges whether the refractive power at the corneal position corresponding to the photodetector position is useful based on a detection result obtained by the corneal-reflection detection unit.

9. An ophthalmic measurement apparatus comprising:
   a projection optical system which projects a slit light bundle onto a fundus of an examinee's eye, the projection optical system scanning the slit light bundle in a predetermined direction;
   a photo-receiving optical system provided with a plurality of photodetectors which are placed in positions approximately conjugate with a cornea of the examinee's eye, the photodetectors being placed in a first meridian direction orthogonal to an optical axis of the photo-receiving optical system and in a second meridian direction orthogonal to the optical axis of the photo-receiving optical system and intersecting with the first meridian direction at a predetermined angle;
   a rotation unit which rotates the scanning direction of the slit light bundle about an optical axis of the projection optical system, and the photodetectors placed in the first and second meridian directions about the optical axis of the photo-receiving optical system, in synchronization with each other; and
   an arithmetic part which obtains, based on a signal indicating a phase difference at the time when one of the photodetectors placed in the first meridian direction photo-receives the slit light bundle and a signal indicating a phase difference at the time when one of the photodetectors placed in the second meridian direction photo-receives the slit light bundle after being rotated by the predetermined angle, the photodetector placed in the second meridian direction being at the same distance from the optical axis of the photo-receiving optical system as the photodetector placed in the first meridian direction, refractive power in two directions at a corneal position corresponding to a position of each photodetector, and further obtains at least one of refractive power and a wavefront inclination by vector-synthesizing the obtained refractive power in the two directions.

10. The ophthalmic measurement apparatus according to claim 9, wherein the arithmetic part obtains, based on a signal indicating a phase difference between a position of the optical axis of the photo-receiving optical system and the photodetector, the refractive power in the two directions at the corneal position corresponding to the photodetector position.

11. The ophthalmic measurement apparatus according to claim 10, further comprising an optical-axis-deviation detection unit which detects deviation of the optical axis of the photo-receiving optical system with respect to one of a corneal center and a visual axis,
wherein the arithmetic part judges whether the refractive power at the corneal position corresponding to the photodetector position is useful based on a detection result obtained by the optical-axis-deviation detection unit.

12. The ophthalmic measurement apparatus according to claim 9, wherein
the second meridian direction is orthogonal to the first meridian direction, and
the arithmetic part obtains, based on the signal indicating the phase difference at the time when the photodetector placed in the first meridian direction photo-receives the slit light bundle and the signal indicating the phase difference at the time when the photodetector placed in the second meridian direction photo-receives the slit light bundle after being rotated by 90°, the photodetector placed in the second meridian direction being at the same distance from the optical axis of the photo-receiving optical system as the photodetector placed in the first meridian direction, the refractive power in the two directions at the corneal position corresponding to the position of each photodetector.

13. The ophthalmic measurement apparatus according to claim 9, further comprising a corneal-reflection detection unit which detects corneal reflection of the slit light bundle,
wherein the arithmetic part judges whether the refractive power at the corneal position corresponding to the photodetector position is useful based on a detection result obtained by the corneal-reflection detection unit.

* * * * *